United States Patent [19]

Sturm

[11] Patent Number: 4,683,332

[45] Date of Patent: Jul. 28, 1987

[54] PARA-NITRODIPHENYLAMINE SYNTHESIS

[75] Inventor: Budd H. Sturm, Hartville, Ohio

[73] Assignee: The Goodyear Tire & Rubber Company, Akron, Ohio

[21] Appl. No.: 735,513

[22] Filed: May 20, 1985

[51] Int. Cl.$^4$ .............................................. C07C 85/02
[52] U.S. Cl. .................................... 564/414; 564/406; 564/433
[58] Field of Search ........................ 564/414, 433, 406

[56] References Cited

U.S. PATENT DOCUMENTS

| | | | |
|---|---|---|---|
| 3,313,854 | 4/1967 | Levy | 564/406 |
| 4,155,936 | 5/1979 | Sturm | 564/414 |
| 4,187,248 | 2/1980 | Merten et al. | 564/414 |
| 4,435,599 | 3/1984 | Sturm | 564/433 |

FOREIGN PATENT DOCUMENTS

| | | | |
|---|---|---|---|
| 641592 | 5/1962 | Canada | 564/406 |
| 3308659 | 9/1984 | Fed. Rep. of Germany | 564/406 |

OTHER PUBLICATIONS

Sidgwick, N. V. "The Organic Chemistry of Nitrogen" Clarendon Press, Oxford 1966, pp. 159–160.

Primary Examiner—Charles F. Warren
Assistant Examiner—John A. Sopp
Attorney, Agent, or Firm—D. O. Nickey

[57] ABSTRACT

There is disclosed a process for the synthesis of para-nitrodiphenylamines via the Formanilide Process wherein the improvement is characterized in that a specific catalyst is utilized. More specifically, a zinc (II) compound (zinc in the plus two oxidation or valence state), is used as a catalyst in the preparation of para-nitrodiphenylamines via the formanilide process.

11 Claims, No Drawings

PARA-NITRODIPHENYLAMINE SYNTHESIS

TECHNICAL FIELD

The present invention is concerned with a catalyst to prepare para-nitrodiphenylamines wherein the catalyst overcomes numerous disadvantages presently found in the production of para-nitrodiphenylamines.

BACKGROUND ART

This invention relates to an improvement in the synthesis of para-nitrodiphenylamines. Para-nitrodiphenylamines are useful intermediates in the formation of rubber antioxidants and antiozonants. Their generic formula is as follows:

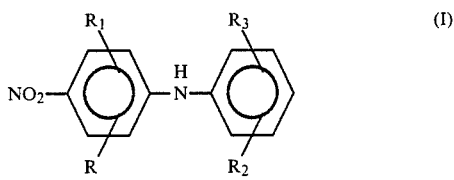

wherein R and $R_1$ are selected from the group consisting of hydrogen radicals and alkyl radicals of 1 to 9 carbon atoms; $R_2$ and $R_3$ are selected from the group consisting of hydrogen radicals, alkyl radicals from 1 to 9 carbon atoms, alkoxy radicals of 1 to 9 carbon atoms and cycloalkyl radicals of 5 to 6 carbon atoms.

Presently, these compounds are synthesized by reacting (1) para-halonitrobenzenes conforming to the following structural formula:

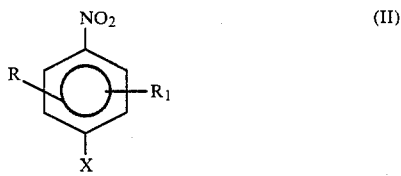

wherein X is a halogen selected from the group consisting of chlorine and bromine; and wherein R and $R_1$ are defined above; (2) with a primary aromatic amine of the following structural formula:

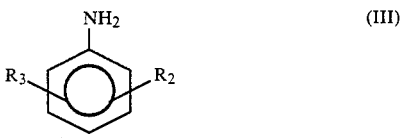

wherein $R_2$ and $R_3$ are defined as above; (3) in the presence of a neutralizing agent, selected from the group consisting of alkali metal salts, oxides of alkali metal salts and alkali metal hydroxides; and (4) in the presence of a catalyst at a concentration of at least 0.1 parts by weight per hundred parts per weight of the para-halonitrobenzene; (5) at a temperature of 120°–250° C.; (6) at a pressure of from atmospheric to about 300 kPa (kilopascals) and (7) with an excess of primary aromatic amine of from 3 to 300 percent.

Presently commerically accepted processes for the production of para-nitrodiphenylamines are described in British Pat. Nos. 798,148; 834,510; German Pat. Nos. 185,663 and 1,056,619; and U.S. Pat. No. 3,155,727. U.S. Pat. No. 4,435,599, by the inventor herein, describes a co-catalyst system for the above described reaction.

Polish Pat. No. 101,496 discloses a method for producing para-nitrodiphenylamines from aniline and para-chloronitrobenzene in the presence of an acid acceptor with concomitant azeotropic water removal using cupric-oxide and dimethylformamide or copper-metal as the catalyst, the improvement being the addition of zinc dust in an amount no larger than 2 percent relative to para-chloronitrobenzene. This Polish patent does not suggest or disclose the use of zinc (II) compounds, (zinc in the plus two oxidation or valence state) to achieve a substantial reduction in the reaction times and provide for increased yield with fewer side reactions.

The presently accepted routes to para-dinitrodiphenylamines (PDNDP) using a p-halonitrobenzene intermediate are the copper catalyzed reactions and the formanilide process. These two routes are different in that the Cu catalyzed reactions require long reaction times (10–24 hours), provide moderate yields of product (75–90%) with less pollution in the waste water than the heretofore mentioned formanilide process.

In the formanilide process, one first reacts formic acid with the primary aromatic amine in the presence of an azeotroping solvent such as toluene. The water of the reaction is azeotroped off at pot temperatures of 125° C. or less. The formanilide produced (such as phenylformamide, $C_6H_5NHCHO$) is then reacted with a p-halonitrobenzene in the presence of a neutralizing agent to yield the p-nitrodiphenylamine, with reaction times of 8–10 hours. A 50% excess of formanilide is required to achieve good yields; however, excessively high COD's in the waste water results.

U.S. Pat. No. 4,155,936 by the present applicant is herein incorporated by reference and made a part hereof. Specifically, U.S. Pat. No. 4,155,936 is concerned with the incorporation of solubilizing agents in the reaction mixture to reduce reaction times and improve yields.

U.S. Pat. No. 4,155,936 and other publications do not suggest or disclose the use of zinc (II) compounds in the preparation of para-nitrodiphenylamines from para-halonitrobenzenes and primary aromatic amines via the formanilide process.

The present invention provides shorter reaction times, lower levels of excess formanilide and neutralizing agent with lower levels of environmentally unsound effluents from the reaction than presently known in the art.

The patents and literature cited do not suggest or disclose the use of any metal catalyst in the formanilide process and the unexpected improvements in the synthesis of para-nitrodiphenylamines that can be obtained.

DISCLOSURE OF THE INVENTION

There is disclosed a process wherein (1) a para-halonitrobenzene conforming to the following structural formula:

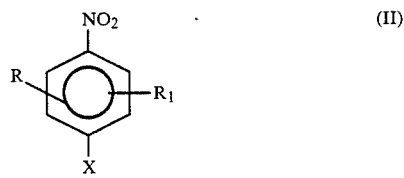

wherein R and R₁ are selected from the group consisting of hydrogen radicals and alkyl radicals of 1 to 9 carbon atoms and wherein X is a halogen selected from the group consisting of chlorine and bromine; is reacted with (2) a formanilide of the following general structural formula:

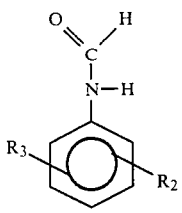

wherein $R_2$ and $R_3$ are selected from the group consisting of hydrogen radicals, alkyl radicals of 1 to 9 carbon atoms and alkoxy radicals of 1 to 9 carbon atoms and cycloalkyl radicals of 5 to 6 carbon atoms; in the presence of (3) a neutralizing agent, selected from the group consisting of alkali metal salts, oxides of alkali metal salts and alkali metal hydroxides; (4) at a temperature of 120°–250° C.; (5) at a pressure from atmospheric to about 300 kPa; (6) with an excess of formanilide; wherein the improvement is characterized in that a catalyst selected from the group comprising (a) zinc (II) salts, (b) zinc (II) oxides, (c) zinc (II) sulfides and (d) organometallic zinc (II) compounds; is added to the reaction mixture.

There is also disclosed a process for producing p-nitrodiphenylamine from formanilide and p-chloronitrobenzene wherein the reaction is conducted (a) at a temperature from 120° to 250° C., (b) in the presence of an alkaline metal salt, (c) with an excess of formanilide, (d) at atmospheric pressure or above, (e) in the presence of a solublizing agent, (f) with at least 0.04 parts by weight per 100 parts by weight of the p-chloronitrobenzene of a catalyst, selected from a group comprising zinc acetate, zinc sulfide, zinc stearate, zinc oxide, zinc chloride, zinc carbonate, zinc cyanide, zinc nitrate, zinc titanate, zinc chromate and zinc dimethyldithiocarbamate.

Representative of the zinc (II) compounds that can be used in the process of the present invention are: zinc acetate, zinc oxide, zinc chloride, zinc sulfide, zinc stearate, zinc nitrate, zinc cyanide, zinc chromate, zinc titanate, zinc sulfate, zinc carbonate, and zinc dimethyldithiocarbamate.

The process of the present invention can be used with or without solubilizing agents as disclosed in U.S. Pat. No. 4,155,936. The work-up of the final product is also described in U.S. Pat. No. 4,155,936.

BEST MODE FOR CARRYING OUT THE INVENTION

The following examples are intended to illustrate and not to limit the scope of the present invention. All the following experiments were carried out in a one liter three-necked flask equipped with a stirrer, dropping funnel, thermometer, and a Claisen adapter connected to a Dean-Stark trap which is connected to a water condenser. Temperature of the reaction pot is controlled by the amount of azeotroping solvent (i.e. toluene) which is added or removed through the Dean-Stark trap.

EXPERIMENT 1

89 gms of aniline and 60 mls of toluene were charged to the reaction system. 50 gms of 90% formic acid was added dropwise over a period of 2-5 minutes with constant stirring. The mixture was heated and the water of the reaction was azeotroped off to maintain a pot temperature of 125° C. or less. The mixture was cooled to below 100° C. To the formanilide formed was charged 100 gms p-nitrochlorobenzene (PCNB), 65 gms anhydrous $K_2CO_3$ and 0.5 gms of zinc $(Ac)_2.2H_2O$ wherein Ac represents an acetate radical. The reaction mixture was heated to 165° C. removing excess toluene through the Dean-Stark trap to maintain a temperature of approximately 165° C. for 5 hours to remove the water of reaction. From the amount of water collected after 5 hours it was determined that the reaction was finished for all practical purposes. The mixture was cooled below 100° C. and 200 mls of toluene was added. The mixture was then hydrolyzed with hot dilute NaOH (30 gms NaOH in 200 ml $H_2O$) or caustic solution at 70°–77° C. for 1½ to 2 hours. The salt cake was removed with the water layer. A second hydrolysis (70°–75° C.) with hot water (200 ml) was usually required to remove the last traces of formanilide from the mixture. The product/toluene solution was then azeotroped to dryness so that organic salts precipitated out and were filtered off. The organic solution was then stripped at a pot temperature of 180° C. at 10-20 mm Hg pressure to yield crude product. The crude product was weighted and analyzed for unreacted PCNB, dinitrotriphenylamine and p-nitrodiphenylamine (product). Crude yield 100%, product analyzed at 96.6% p-nitrodiphenylamine, 3.3% dinitrodiphenylamine, and 0.7% PCNB.

EXPERIMENTS 2-14

The procedure described in Experiment 1 was followed except that the type and amount of $Zn^{++}$ compound and the reaction time was varied. Also several experiments using a solubilizing agent are presented together with controls.

Table I contains the percent true yield of product and by-products for Experiment 1-24.

TABLE I

| Exp. | Catalyst wt % on 100 gms PCNB | Solubilizing Agent (gms) | Reaction Time (Hours) at 165° C. | % Excess Formanilide | % Excess $K_2CO_3$ | % PCNB | % DNTPA | % True Yield (a), (b) p-$NO_2$DPA |
|---|---|---|---|---|---|---|---|---|
| 1 | $Zn(Ac)_2.H_2O$ 0.5% | none | 5 | 50 | 30 | 0.7 | 3.3 | 96.6 |
| 2 | $Zn(Ac)_2.H_2O$ 2.0% | none | 5.5 | 50 | 30 | 0.7 | 3.7 | 94.8 |
| 3 | ZnS 0.4% | none | 6 | 25 | 15 | 1.5 | 3.2 | 89.8 |
| 4 | $ZnCrO_4$ 0.4% | none | 8 | 25 | 15 | 0.7 | 4.0 | 92.9 |
| 5 | $ZnTiO_3$ | none | 7 | 25 | 15 | 1.1 | 5.4 | 93.5 |

TABLE I-continued

| Exp. | Catalyst wt % on 100 gms PCNB | Solubilizing Agent (gms) | Reaction Time (Hours) at 165° C. | % Excess Formanilide | % Excess K$_2$CO$_3$ | % PCNB | % DNTPA | % True Yield (a), (b) p-NO$_2$DPA |
|---|---|---|---|---|---|---|---|---|
| 6 | 0.4% ZnS | none | 8 | 10 | 6 | 1.9 | 6.8 | 85.6 |
| 7 | 0.4% ZnSO$_4$.7H$_2$O | none | 8 | 10 | 6 | 1.5 | 6.3 | 85.8 |
| 8 | 0.4% Zn(NO$_3$)$_2$.6H$_2$O | none | 8 | 25 | 15 | 1.3 | 5.0 | 93.9 |
| 9 | 1.0% Zn(CN)$_2$ | none | 6 | 25 | 15 | 1.0 | 6.1 | 92.0 |
| 10 | 0.5% Zn Stearate | none | 8.5 | 25 | 15 | 0.7 | 5.4 | 93.1 |
| 11 | 0.5% ZnCl | none | 7.5 | 25 | 15 | 2.1 | 5.3 | 91.4 |
| 12 | 0.5% Zn Stearate | none | 8.5 | 10 | 6 | 2.5 | 6.9 | 85.7 |
| 13 | 1.0% Zn Stearate | none | 9 | 10 | 6 | 3.3 | 6.2 | 84.0 |
| 14 | 0.5% ZnO | none | 5.5 | 50 | 30 | 0.7 | 3.7 | 94.8 |
| 15 | 2.0% Zn(Ac)$_2$.2H$_2$O | none | 3.5 | 50 | 30 | 4.7 | 2.1 | 88.9 |
| 16 | 0.66% Zn(Ac)$_2$.2H$_2$O | 2% M-5000* | 3 | 50 | 30 | 2.8 | 3.3 | 91.0 |
| 17 | 0.66% Zn(Ac)$_2$.2H$_2$O | 2% M-5000* | 7.5 | 5.0 | 10–12% | 4.5 | 9.0 | 84.5 |
| 18 | 0.66% Zn(Ac)$_2$.2H$_2$O | 2% M-5000* | 9 | 5.0 | 10–12% | 4.4 | 7.7 | 80.2 |
| 19 | 2.0% Zn(Ac)$_2$.2H$_2$O | 2% M-5000* | 8 | 5.0 | 10–12% | 5.0 | 7.6 | 80.5 |
| 20 | 0.04% Zn(Ac)$_2$.2H$_2$O | none | 4 | 50 | 30 | 2.4 | 3.0 | 92.2 |
| 21 | 1.0% Zn(Ac)$_2$.2H$_2$O | none | 4 | 50 | 30 | 1.0 | 3.6 | 92.9 |
| 22 | 2% Zn(Ac)$_2$.2H$_2$O | none | 6.5 | 25 | 15 | 3.4 | 4.2 | 86.7 |
| 23 | 0.5% Zn(Ac)$_2$.2H$_2$O | none | 9 | 10 | 6 | 4.2 | 6.0 | 81.3 |
| 24 | 1.0% Zn Stearate | none | 21 | 50 | 30 (NaCO$_3$) | 4.5 | 4.0 | 66.2 |
| CONTROLS |||||||||
| 25 | none | none | 8.5 | 50 | 30 | 0.4 | 3.0 | 96.2 |
| 26 | none | none | 8.5 | 25 | 15 | 1.0 | 5.9 | 90.5 |
| 27 | none | none | 8.25 | 10 | 6 | 2.6 | 9.8 | 81.2 |
| 28 | Zn° dust | none | 8.5 | 50 | 30 | — | 2.2 | 92.4 |
| 29 | 0.5% Zn° dust | none | 9 | 50 | 30 | 0.5 | 2.1 | 84.1 |
| 30 | 2.0% Zn° dust | none | 8.5 | 25 | 15 | 1.0 | 3.4 | 83.9 |
| 31 | 0.5% Zn° dust | none | 9 | 25 | 15 | 3.3 | 3.1 | 77.4 |
| 32 | 2.0% Zn° dust | none | 9 | 10 | 6 | 4.2 | 2.6 | 77.2 |
| 33 | 0.5% Zn° dust 2.0% | none | 9 | 10 | 6 | 3.4 | 3.5 | 73.5 |

*M-5000 is Union Carbide's Carbowax Methoxy PEG-5000
(a)True Yield p-NO$_2$DPA = % Crude Yield times % p-NO$_2$DPA/100
(b)p-NO$_2$DPA is para-nitrodiphenylamine, determined by LC Bonded Nitrile Column, Method AR-396

From Experiments 25, 26 and 27 (controls, no catalysts), it is evident that as excess formanilide and K$_2$CO$_3$ are lowered, the yield of p-NO$_2$DPA decreases.

From Experiments 1–24, it is evident that small amounts of Zn$^{++}$ compounds accelerated the reaction when compared to the controls. The best level of Zn$^{++}$ appears to be less than 2%.

From Experiments 28–33 (Controls/Zn° dust), it is evident that Zn° dust is detrimental to the formanilide reaction. The more Zn° dust used, the lower the yield of p-NO$_2$DPA.

A comparison of Experiment 26 (Control) with Experiments 3, 4 and 5 demonstrate that the catalyst of this invention provides higher yields of product in a shorter reaction time with less excess of reagents. The same is true from a comparison of Experiment 2 with Experiments 6 and 7.

Experiment 3 had 1.5% PCNB left in the reaction mixture vs. 1.0% in Experiment 26. Had the reaction been run an extra 0.5 to 1.0 hours longer, the yield of p-NO$_2$DPA would have increased. Thus, the presence of Zn° dust is detrimental to the formanilide process while Zn$^{++}$ gives benefits.

A comparison of Experiments 26 and 27 with Experiments 8–13 further demonstrates the benefits of the instant invention.

While certain representative embodiments and details have been shown for the purpose of illustrating the invention, it will be apparent to those skilled in the art that various changes and modifications may be made herein without departing from the scope of the invention.

What is claimed:

1. A process wherein (1) a para-halonitrobenzene conforming to the following structural formula:

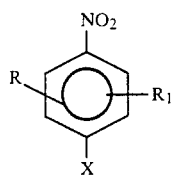

wherein R and R₁ are selected from the group consisting of hydrogen radicals and alkyl radicals of 1 to 9 carbon atoms and wherein X is a halogen selected from the group consisting of chlorine and bromine; is reacted with (2) a formanilide of the following general structural formula:

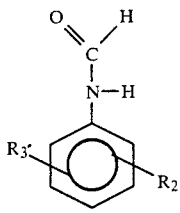

wherein R₂ and R₃ are selected from the group consisting of hydrogen radicals, alkyl radicals of 1 to 9 carbon atoms and alkoxy radicals of 1 to 9 carbon atoms and cycloaklyl radicals of 5 to 6 carbon atoms; in the presence of (3) a neutralizing agent, selected from the group consisting of alkali metal salts, oxides of alkali metal salts and alkali metal hydroxides; (4) at a temperature of 120°–250° C.; (5) at a pressure from atmospheric to about 300 kPa; (6) with an excess of formanilide; wherein the improvement is characterized in that a catalyst is added to the formanilide/p-halonitrobenze reaction selected from the group consisting of (a) zinc (II) salts, (b) zinc (II) oxides, (c) zinc (II) sulfides and (d) organometallic zinc (II) compounds.

2. The process according to claim 1 wherein the formanilide compound is phenylformamide.

3. The process of claim 1 wherein the catalyst is at least one zinc (II) compound selected from the group consisting of zinc acetate, zinc sulfide, zinc stearate, zinc chloride, zinc oxide, zinc carbonate, zinc dimethyldithiocarbamate, zinc cyanide, zinc nitrate, zinc titanate and zinc chromate.

4. The improved process recited in claim 1 wherein a solubilizing agent is incorporated into the reaction mixture at a concentration of 0.25 to 4 parts by weight on 100 parts halo-p-nitrobenzene.

5. A process wherein (1) a para-halonitrobenzene conforming to the following structural formula:

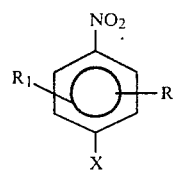

wherein R and R₁ are selected from the group consisting of hydrogen and alkyl radicals of 1 to 9 carbon atoms and wherein X is a halogen selected from the group consisting of chlorine and bromine is reacted; with (2) a formanilide of the following structural formula:

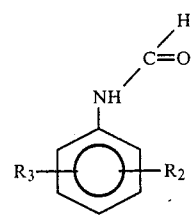

wherein R₂ and R₃ are radicals selected from the group consisting of hydrogen, alkyl radicals of 1 to 9 carbon atoms, alkoxy radicals of 1 to 9 carbon atoms and cycloalkyl radicals of 5 to 6 carbon atoms; (3) in the presence of a neutralizing agent selected from the group consisting of alkaline metal hydroxides; (4) at a temperature of 100° to 250° C. (5) at a pressure from atmospheric to about 300 kPa, (6) with an excess of formanilide, and (7) a solubilizing agent, wherein the improvement is characterized in that a catalyst selected from the group consisting of zinc (II) salts, zinc (II) oxides, zinc (II) sulfides and organometallic zinc (II) compounds; is used.

6. The process according to claim 5 wherein the formanilide compound is phenylformamide.

7. The process of claim 5 wherein the catalyst is selected from the group consisting of zinc acetate, zinc sulfide, zinc stearate, zinc oxide and zinc chloride.

8. The improved process recited in claim 5 wherein a solubilizing agent is incorporated into the reaction mixture at a concentration of 0.25 to 4 parts by weight on 100 parts of halo-para-nitrobenzene.

9. A process for producing p-nitrodiphenylamine from a formanilide and p-chloronitrobenzene wherein the reaction is conducted (a) at a temperature from 100° to 250° C., (b) in the presence of an alkaline metal salt, (c) with an excess of formanilide, (d) at atmospheric pressure or above, (e) in the presence of a solubilizing agent, (f) with at least 0.04 parts by weight per 100 parts by weight of p-chloronitrobenzene of a catalyst selected from a group consisting of zinc acetate, zinc sulfide, zinc stearate, zinc oxide, zinc chloride, zinc carbonate and zinc dimethjyldithiocarbamate.

10. A process according to claim 9 wherein the catalyst is zinc acetate at a concentration of at least 0.08 parts based on 100 parts of p-chloronitrobenzene.

11. A process according to claim 9 wherein the catalyst system is from 0.08 to 1 parts by weight based on 100 parts of the p-chloronitrobenzene.

* * * * *

UNITED STATES PATENT AND TRADEMARK OFFICE
CERTIFICATE OF CORRECTION

PATENT NO. : 4,683,332

DATED : July 28, 1987

INVENTOR(S) : Sturm

It is certified that error appears in the above-identified patent and that said Letters Patent is hereby corrected as shown below:

At Col. 2, line 15 delete "para-dinitrodi-" and insert therefor -- para-nitrodi- --.

At Col. 2, line 16 delete "(PDNDP)" and insert therefor --(PNDP)--.

At Col. 7, line 45 delete "formanilide/p-halonitrobenze" and insert therefor --formanilide/p-halonitrobenzene--.

Signed and Sealed this

Eighth Day of November, 1988

Attest:

DONALD J. QUIGG

Attesting Officer

Commissioner of Patents and Trademarks